(12) United States Patent
Leuthardt et al.

(10) Patent No.: US 10,743,891 B2
(45) Date of Patent: Aug. 18, 2020

(54) DISCECTOMY INSTRUMENT

(71) Applicant: WASHINGTON UNIVERSITY, St. Louis, MO (US)

(72) Inventors: Eric C. Leuthardt, St. Louis, MO (US); Neill Wright, St. Louis, MO (US); Dan Moran, St. Louis, MO (US); Ivan Stoev, St. Louis, MO (US); Tim Johnson, St. Louis, MO (US); Benton Reynolds, St. Louis, MO (US)

(73) Assignee: Washington University, St. Louis, MO (US)

( * ) Notice: Subject to any disclaimer, the term of this patent is extended or adjusted under 35 U.S.C. 154(b) by 396 days.

(21) Appl. No.: 15/647,724

(22) Filed: Jul. 12, 2017

(65) Prior Publication Data

US 2018/0014837 A1 Jan. 18, 2018

Related U.S. Application Data

(60) Provisional application No. 62/361,756, filed on Jul. 13, 2016.

(51) Int. Cl.
| | |
|---|---|
| *A61B 17/16* | (2006.01) |
| *A61B 17/32* | (2006.01) |
| *A61B 17/3205* | (2006.01) |
| *A61B 17/17* | (2006.01) |
| *A61B 17/00* | (2006.01) |
| *A61B 17/22* | (2006.01) |

(52) U.S. Cl.
CPC .......... *A61B 17/1671* (2013.01); *A61B 17/32* (2013.01); *A61B 17/3205* (2013.01); *A61B 17/320016* (2013.01); *A61B 17/1631* (2013.01); *A61B 17/1633* (2013.01); *A61B 17/1659* (2013.01); *A61B 17/1757* (2013.01); *A61B 2017/00261* (2013.01); *A61B 2017/22082* (2013.01); *A61B 2017/320008* (2013.01); *A61B 2017/320052* (2013.01)

(58) Field of Classification Search
CPC ........ A61B 2017/00261; A61B 17/885; A61B 17/22; A61B 17/3205; A61B 17/1671
See application file for complete search history.

(56) References Cited

U.S. PATENT DOCUMENTS

| | | | |
|---|---|---|---|
| 7,309,338 B2 | 12/2007 | Cragg | |
| 7,738,969 B2* | 6/2010 | Bleich | A61B 17/1671 600/373 |
| 8,353,909 B2* | 1/2013 | Michelson | A61B 17/1757 606/53 |
| 8,382,841 B2 | 2/2013 | Yundt | |

(Continued)

*Primary Examiner* — David W Bates
(74) *Attorney, Agent, or Firm* — Armstrong Teasdale LLP (57) ABSTRACT

A discectomy instrument for use with a cutting tool including a flexible shaft and an implement extending from the shaft generally includes a guard including a shaft and a foot extending therefrom, wherein the foot has a port and a plurality of teeth. The instrument also includes a guide including a rod, a finger extending from the rod, and an actuator operably connected to the finger such that the finger is adjustable via the actuator. The instrument further includes a sheath including at least one channel, wherein, when the guide and the sheath are coupled to the guard, the channel aligns with the port to permit insertion of the implement through the port via the channel.

18 Claims, 6 Drawing Sheets

(56) References Cited

U.S. PATENT DOCUMENTS

| | | |
|---|---|---|
| 8,852,243 B2 | 10/2014 | Morgenstern et al. |
| 2003/0191474 A1* | 10/2003 | Cragg ................ A61B 17/1757 606/79 |
| 2004/0127963 A1* | 7/2004 | Uchida .............. A61B 17/1671 607/96 |
| 2005/0203527 A1* | 9/2005 | Carrison ............ A61B 17/1604 606/80 |
| 2005/0209622 A1* | 9/2005 | Carrison ............ A61B 17/1671 606/170 |
| 2006/0184188 A1* | 8/2006 | Li ...................... A61B 17/1617 606/180 |
| 2007/0027464 A1* | 2/2007 | Way .................. A61B 10/0275 606/170 |
| 2008/0195081 A1 | 8/2008 | Moll |
| 2011/0087257 A1* | 4/2011 | To ...................... A61B 17/1617 606/170 |
| 2011/0112373 A1 | 5/2011 | Ainsworth et al. |
| 2011/0313529 A1* | 12/2011 | Schaller ........... A61B 17/32002 623/17.16 |
| 2012/0184910 A1 | 7/2012 | Woehr |
| 2013/0018376 A1* | 1/2013 | Yoon .................. A61B 17/1617 606/79 |
| 2013/0197551 A1* | 8/2013 | Yoon ................. A61B 17/32002 606/170 |
| 2013/0211438 A1* | 8/2013 | Dubois .................. A61B 17/32 606/171 |
| 2014/0276832 A1* | 9/2014 | Hibri ................. A61B 17/1671 606/79 |
| 2014/0303730 A1* | 10/2014 | McGuire ........ A61B 17/320708 623/17.12 |
| 2015/0080896 A1* | 3/2015 | To ................... A61B 17/320016 606/79 |
| 2016/0030060 A1* | 2/2016 | Tally .................. A61B 17/1671 606/84 |
| 2018/0064461 A1* | 3/2018 | Tran ................ A61B 17/32002 |

* cited by examiner

DISCECTOMY INSTRUMENT

CROSS-REFERENCE TO RELATED APPLICATION

This application claims priority to U.S. Provisional Patent Application No. 62/361,756 entitled DISCECTOMY INSTRUMENT filed Jul. 13, 2016, which is hereby incorporated by reference in its entirety.

BACKGROUND

The present disclosure relates generally to surgical instruments and, more particularly, to an instrument for use in performing a lumbar discectomy.

It can be time consuming and challenging to perform a discectomy using conventional instruments. For example, the thecal sac can obstruct the desired point of entry into the disc space between the vertebrae, and it can be difficult to move the thecal sac aside and then shield the thecal sac while cutting tools are inserted into the disc space. Additionally, conventional cutting tools can be difficult to maneuver when removing sections of the disc and/or abrading sections of its adjacent vertebrae.

It would be useful, therefore, to provide an improved instrument for performing a lumbar discectomy.

SUMMARY

In one aspect, a discectomy instrument includes a flexible shaft and an implement extending from the shaft. The instrument generally comprises a guard comprising a shaft and a foot extending therefrom. The foot comprising a port and a plurality of teeth. A guide comprises a rod, a finger extending from the rod, and an actuator operably connected to the finger such that the finger is adjustable via the actuator. A sheath comprises at least one channel. The guide and the sheath are coupled to the guard. The channel aligns with the port to permit insertion of the implement through the port via the channel.

In another aspect, a method for performing a discectomy procedure on a patient generally comprises inserting into the patient a guard comprising a shaft and a foot extending therefrom. The foot comprises a port and a plurality of teeth. A guide is positioned relative to the guard. The guide comprises a rod, a finger extending from the rod, and an actuator operably connected to the finger such that the finger is adjustable via the actuator. A sheath is positioned relative to the guard and the guide. The sheath comprises at least one channel. A cutting tool passes through the channel of the sheath and the port of the guard.

In still another aspect, a discectomy instrument for use with a cutting tool includes a flexible shaft and an implement extending from the shaft. The instrument comprises a guard comprising a shaft and a foot extending therefrom. The foot comprises a port and a plurality of teeth. A guide comprises a rod, a finger extending from the rod, and an actuator operably connected to the finger such that the finger is adjustable via the actuator. A sheath comprises a plurality of proximal channels that converge into a single distal channel that is laterally aligned with the port of the foot. The guide and the sheath can be coupled to the guard. The single distal channel of the sheath aligns with the port of the foot of the guard.

BRIEF DESCRIPTION OF THE DRAWINGS

FIG. 4b is a top view of the sheath shown in FIG. 4a;

Corresponding reference characters indicate corresponding parts throughout the several views of the drawings.

DETAILED DESCRIPTION OF THE DRAWINGS

Figure 1:
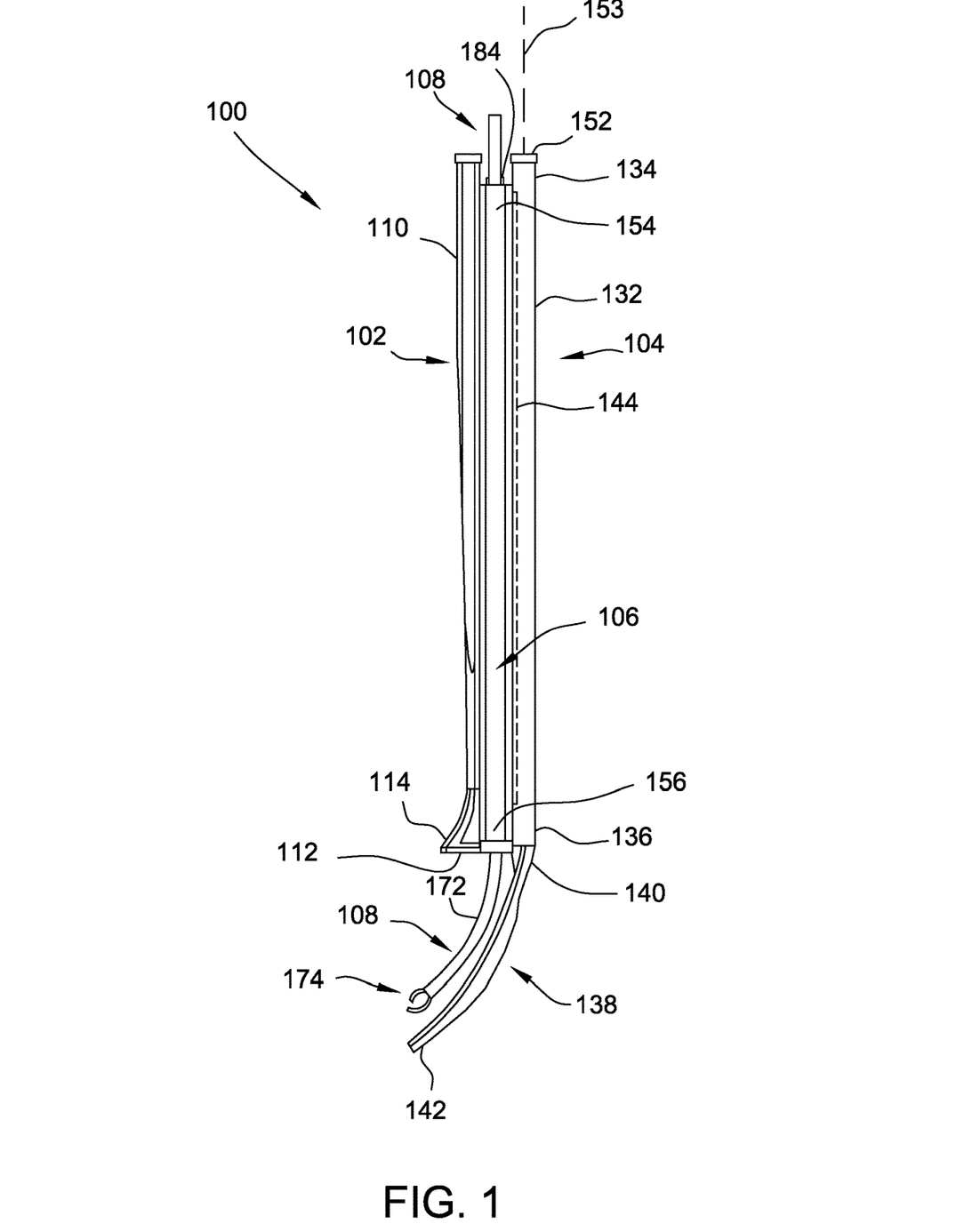
FIG. 1 is a side view of an instrument for use in performing a discectomy, the instrument having a guard, a guide, and a sheath.

FIG. 1 illustrates one suitable embodiment of a discectomy instrument (indicated generally at 100) suitable for use in lumbar discectomy procedures. In the illustrated embodiment, the instrument 100 includes: a guard 102; a guide 104 configured for coupling to the guard 102; and a sheath 106 configured for coupling to the guide 104 and seating between the guard 102 and the guide 104. A cutting tool 108 is sized and shaped for insertion through the sheath 106, and thus is suitable for use with the instrument 100. In other embodiments, the instrument 100 may have any suitable number of components coupled together in any suitable manner that enables the instrument 100 to function as described herein.

Figure 2:
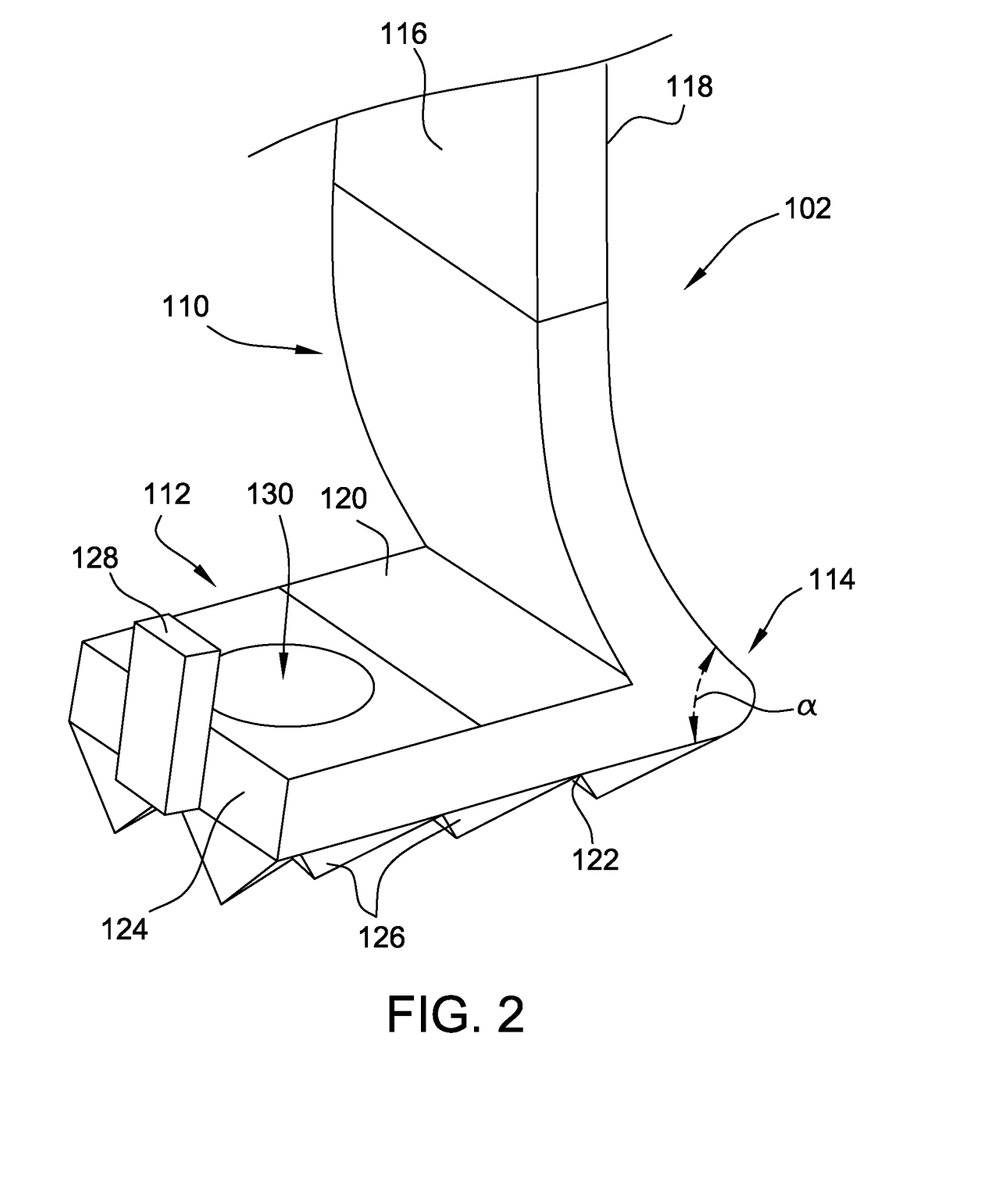
FIG. 2 is an enlarged, fragmented perspective view of the guard of the instrument shown in FIG. 1.

Referring now to FIGS. 1 and 2, the illustrated guard 102 includes a shaft 110 and a foot 112 extending from the shaft 110 at a joint 114 such that the guard 102 is generally L-shaped. The shaft 110 has an inner surface 116 and an outer surface 118, and the foot 112 has an inner surface 120 and an outer surface 122. The outer surface 118 of the shaft 110 is oriented at an acute angle α (e.g. about 45°) relative to the outer surface 122 of the foot 112 at the joint 114 such that the joint 114 has an exterior profile that is wedge-shaped. The illustrated foot 112 also has: a tip (or distal end) 124; a plurality of teeth 126 (or spikes) extending outward from the outer surface 122; a tab 128 outboard of the tip 124; and a port 130 extending from the inner surface 120 to the outer surface 122 such that the port 130 extends through the thickness of the foot 112.

In other embodiments, the joint 114 may not have a wedge-shaped profile, and/or the tab 128 may extend inward from any suitable location (i.e., the tab 128 may not be located near the tip 124 in some embodiments). Although the shaft 110 and the foot 112 are integrally formed together as a single-piece, unitary structure in the illustrated embodiment, the foot 112 may be suitably coupled to the shaft 110 in other embodiments (i.e., the foot 112 and the shaft 110 may be separately formed structures that are attached together using a suitable mechanism and/or bonding agent).

Figure 3:
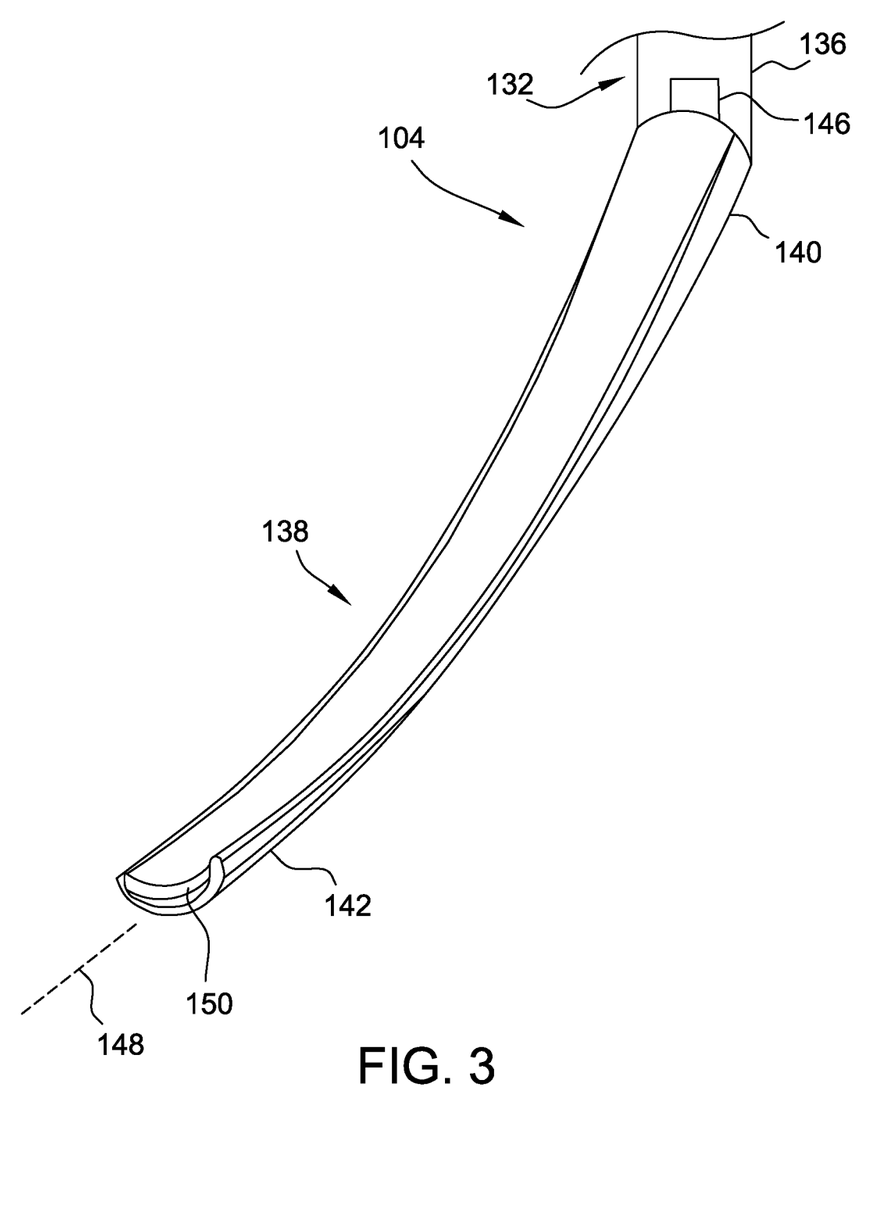
FIG. 3 is an enlarged, fragmented perspective view of the guide of the instrument shown in FIG. 1.

With reference to FIGS. 1 and 3, the guide 104 includes: a rod 132 having a proximal end 134 (shown in FIG. 1) and a distal end 136; and a finger 138 having a proximal end 140 and a distal end 142. The rod 132 also has: a groove 144 (shown in FIG. 1) that extends between the proximal end 134 and the distal end 136; and a slot 146 located at the distal end 136 and sized to receive the tab 128 of the guard 102. The proximal end 140 of the finger 138 is attached to the distal end 136 of the rod 132, such that the finger 138 extends from the rod 132 to its distal end 142 along a lengthwise axis 148. Although the finger 138 is attached to the rod 132 in the illustrated embodiment, the finger 138 and the rod 132 may be integrally formed together as a single-piece, unitary structure in other embodiments.

In the illustrated embodiment, the finger 138 has a chute-like shape, in that the finger 138 is curved along the lengthwise axis 148 and has a generally U-shaped (or scalloped) cross-sectional profile 150 along a plane oriented substantially perpendicular to the lengthwise axis 148. Moreover, the finger 138 is made of a flexible material, and the finger 138 is operably coupled to an actuator (e.g., a dial 152 positioned at the proximal end 134 of the rod 132 as shown in FIG. 1) such that the finger 138 can be articulated. In this manner, the curvature of the finger 138 along the lengthwise axis 148 is adjustable (i.e., the curvature of the lengthwise axis 148 is adjustable) by operating the actuator. For example, a surgeon may rotate the dial 152 in one direction to make the finger 138 more curved along its length, or may rotate the dial 152 in the opposite direction to make the finger 138 more flat along its length. In other embodiments, the finger 138 may have any suitable profile 150 (e.g., the profile 150 may be V-shaped in some embodiments). Alternatively, the finger 138 may not be made of a flexible material, the actuator may be located anywhere along (or remote from) the rod 132, and/or the finger 138 may not be articulated.

Figure 4A:
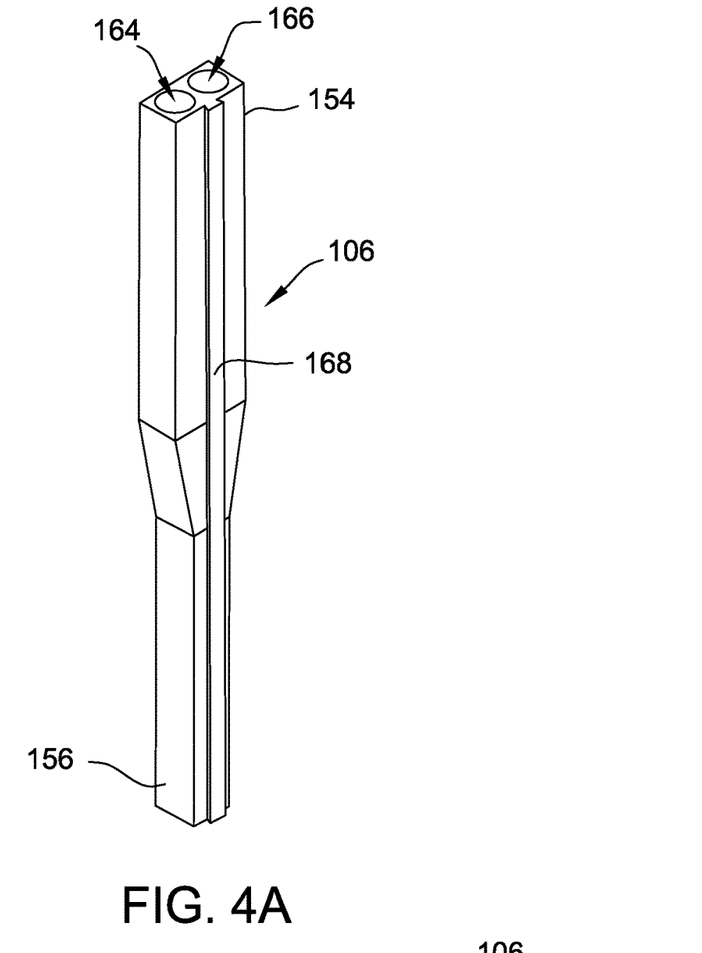
FIG. 4a is a perspective view of the sheath of the instrument shown in FIG. 1.
Figure 4B:
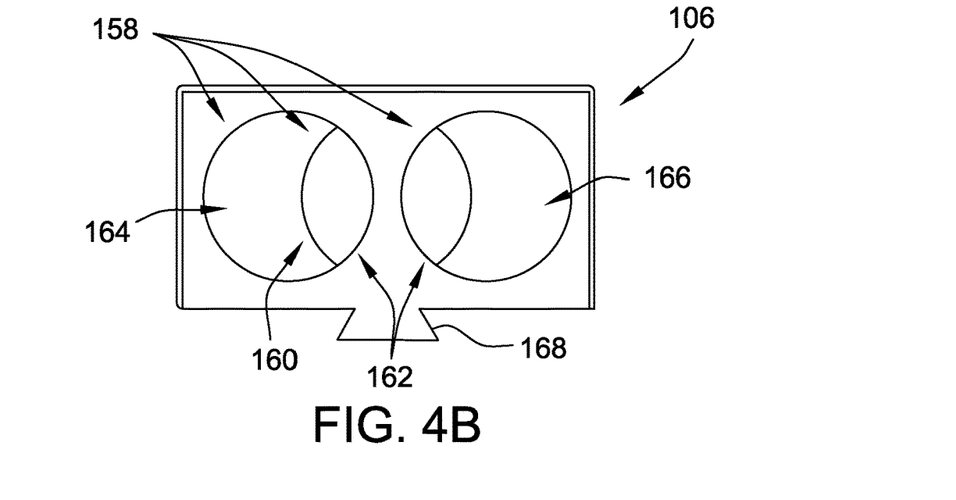

Referring now to FIGS. 1, 4a, and 4b, the sheath 106 is a generally tubular structure having a proximal end 154, a distal end 156, and at least one channel 158 extending from the proximal end 154 to the distal end 156. For example, in the illustrated embodiment, the sheath 106 has a distal channel 160 that is accessible via the distal end 156, and a plurality of proximal channels 162 (e.g., a first proximal channel 164 and a second proximal channel 166) that are accessible via the proximal end 154 such that the proximal channels 162 converge into the distal channel 160 between the proximal end 154 and the distal end 156. Moreover, the sheath 106 also has an exterior rib 168 that extends between the proximal end 154 and the distal end 156, and is sized for insertion into the groove 144 of the guide 104 along a longitudinal axis 153 (shown in FIG. 1) of the guide 104, such that the rib 168 and the groove 144 mate with one another to prevent lateral separation of the sheath 106 from the guide 104 (i.e., once the rib 168 is slid longitudinally into the groove 144, the sheath 106 and the guide 104 can only be separated by sliding the rib 168 longitudinally out of the groove 144).

Figure 5A:
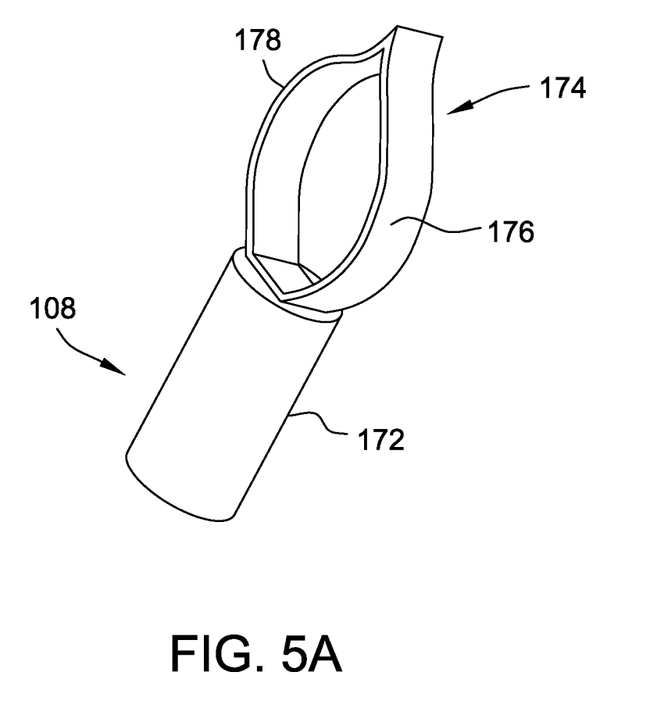
FIG. 5a is a perspective view of one embodiment of a cutting tool suitable for use with the instrument shown in FIG. 1.
Figure 5B:
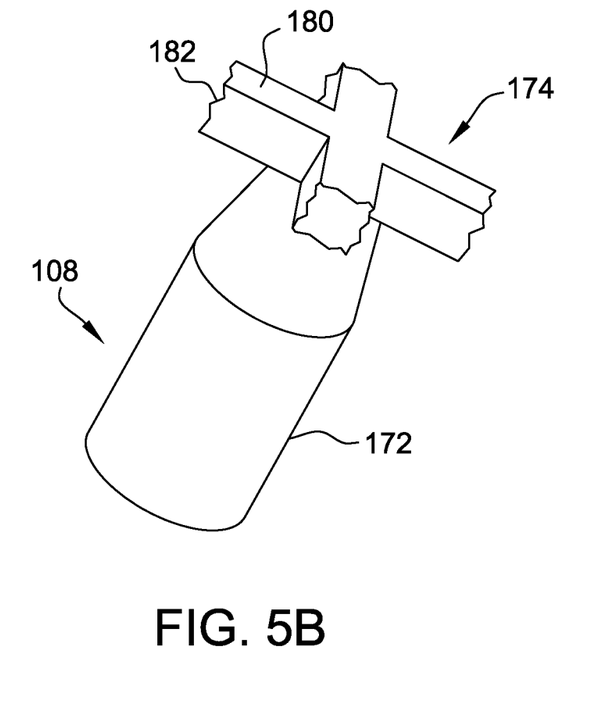
FIG. 5b is a perspective view of another embodiment of a cutting tool suitable for use with the instrument shown in FIG. 1.

As illustrated in FIGS. 5a and 5b, the cutting tool 108, which is suitable for use with the instrument 100, has: a flexible shaft 172 (e.g., the shaft 172 may be made of a wire that is counter-wound tightly into coils); and an implement 174 attached to the shaft 172. In the embodiment of FIG. 5a, the implement 174 includes at least one blade 176 having a sharp edge 178 for removing softer tissue such as disc tissue (e.g., the blade(s) 176 may be strip-type blade(s) formed into an eggbeater-like shape as shown). In the embodiment of FIG. 5b, the implement 174 alternatively includes at least one abrasive member 180 for removing harder tissue such as bone tissue (e.g., the implement 174 may have a plurality of abrasive members 180 in the form of arms arranged in a propeller-like manner, and each having a roughened tip 182). In some embodiments, the implement 174 may be detachable from the shaft 172. In that regard, the cutting tool 108 may be provided with a kit of implements 174 that are interchangeably attachable to the shaft 172, and each implement 174 in the kit may be disposable. In other embodiments, the implement 174 may have any suitable tissue-removal structure (e.g., the implement 174 may be a wire brush such as, for example, a rotating-type wire brush) and/or may not be detachable from the shaft 172.

Figure 6:
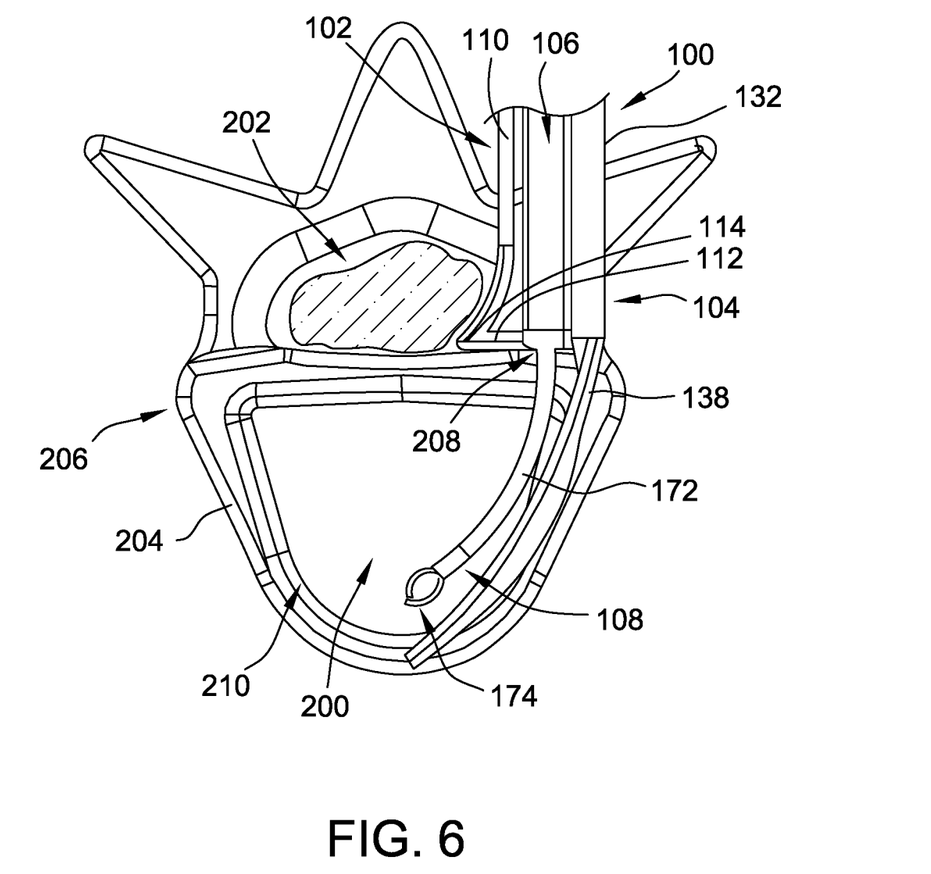
FIG. 6 is a schematic illustration of the instrument shown in FIG. 1 in use during a discectomy, only a portion of the instrument being seen.

Referring now to FIG. 6, the instrument 100 may be used in a variety of discectomy procedures such as, for example, in a full lumbar discectomy to remove the more difficult-to-reach segments of a disc 200, after the easier-to-reach segments of the disc 200 have already been removed by microdiscectomy. More specifically, to use the instrument 100, the wedge-shaped joint 114 of the guard 102 is first manipulated to gently move the thecal sac 202 aside, and the teeth 126 of the foot 112 are then firmly seated (or anchored) against a vertebra 204 of the patient's spinal column 206 such that the port 130 is positioned over a desired point of entry 208 into the associated disc space 210.

With the foot 112 seated against the vertebra 204, the guide 104 is coupled to the foot 112 such that the tab 128 of the foot 112 is inserted into the slot 146 of the guide 104. The sheath 106 is then coupled between the shaft 110 of the guard 102 and the rod 132 of the guide 104 by inserting the rib 168 of the sheath 106 into the groove 144 of the guide 104, and sliding the sheath 106 longitudinally along the rod 132 of the guide 104 until the distal end 156 of the sheath 106 is seated against the foot 112 of the guard 102, with the distal channel 160 of the sheath 106 laterally aligned with the port 130 of the guard 102 (and, hence, laterally aligned with the desired point of entry 208 into the disc space 210). In this manner the guide 104 is laterally fixed to the guard 102, and the sheath 106 is laterally fixed to the guide 104, such that lateral separation of the components is inhibited during use.

With the guard 102, the guide 104, and the sheath 106 coupled together as set forth above, the cutting tool 108 (having an appropriate implement 174 coupled to the shaft 172) is inserted into either the first proximal channel 164 or the second proximal channel 166 of the sheath 106 such that the implement 174 passes through the distal channel 160 of the sheath 106 and through the port 130 of the guard 102, into the disc space 210 via the point of entry 208. Optionally, the cutting tool 108 and/or the sheath 106 may have an adjustable slide-stop or gauge (e.g., an adjustable stop ring 184) that facilitates regulating how far the cutting tool 108 is insertable into the sheath 106 and, hence, regulating how far the implement 174 can protrude from the sheath 106, thereby regulating the depth at which the cutting tool 108 is insertable into the disc space 210.

With the implement 174 inserted into the disc space 210, the cutting tool 108 is suitably operable (e.g., rotatable) to remove the softer tissue of the disc 200 and/or the harder tissue of the adjacent vertebra 204. Notably, the finger 138 of the guide 104 facilitates directing the cutting tool 108 into different areas of the disc space 210. More specifically, the profile 150 of the finger 138 facilitates keeping the implement 174 from straying off a desired course, and the adjustable curvature of the finger 138 (e.g., via the dial 152) provides the surgeon with enhanced coverage and control when accurately and precisely moving the implement 174 from one area of the disc space 210 to another. In this manner, the guard 102 and the sheath 106 facilitate shielding the thecal sac 202 from the implement 174 (and the teeth 126) when the instrument 100 is in use, thereby mitigating morbidity of the thecal sac 202 as a result of the discectomy procedure. Moreover, when using multiple different cutting tools 108, and/or a cutting tool 108 with interchangeable implements 174, the surgeon may choose a blade-like implement 174 (FIG. 5a), an abrasive implement 174 (FIG. 5b), or any other suitable implement (e.g., a rotating-type wire brush implement) for insertion into the disc space 210 to respectively cut softer disc tissue, grind harder vertebra tissue, or perform any other suitable type of tissue-removal step in the overall procedure.

Because the sheath 106 has a plurality of proximal channels 162 that converge into a single distal channel 160 that is laterally aligned with port 130 and the desired point of entry 208, the surgeon can have multiple surgical tools of different types (e.g., cutting tool(s), a suction tool, etc.) simultaneously inserted into the sheath 106 to provide a more instantaneous and interchangeable deployment of such tools into the disc space 210 via the port 130. For example, in one instance, the cutting tool 108 may be inserted into the first proximal channel 164, while a suction hose (not shown) is simultaneously inserted into the second proximal channel 166, such that each is selectively insertable into the disc space 210. More specifically, the surgeon may insert the cutting tool 108 into the disc space 210 for removing tissue, and then retract the implement 174 into the first proximal channel 164 before inserting the suction hose into the disc space 210 to clear the removed tissue from the disc space 210. After the disc space 210 is sufficiently cleared of removed tissue, the suction hose may then be retracted into the second proximal channel 166, before reinserting the cutting tool 108 into the disc space 210 for removing more tissue. This process is repeatable as desired.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A discectomy instrument comprising:
   a guard comprising a shaft and a foot extending therefrom, wherein the foot comprises a first surface, a second surface in opposed relationship with the first surface, a port extending through the foot from the first surface to the second surface, and a plurality of teeth extending outward from the second surface;
   a guide comprising a rod, a finger extending from the rod, and an actuator operatively connected to the finger such that the finger is selectively articulated via the actuator, the rod including a groove; and
   a sheath comprising at least one channel and an exterior rib, the exterior rib being sized and shaped for insertion into the groove of the rod of the guide, and the sheath being selectively coupled to the shaft of the guard so that the channel of the sheath aligns with the port in the foot of the guard to permit insertion of an implement through the port via the channel.

2. The discectomy instrument set forth in claim 1, wherein the foot of the guard includes a tip and a tab disposed on the tip.

3. The discectomy instrument set forth in claim 2, wherein the rod of the guide includes a proximal end and a distal end and a slot located at the distal end, the slot being sized and shaped to receive the tab of the guard.

4. The discectomy instrument set forth in claim 3, wherein the finger of the guide is attached to the distal end of the rod.

5. The discectomy instrument set forth in claim 1, wherein the sheath is positioned between the shaft of the guard and the rod of the guide, the exterior rib of the sheath being inserted into the groove of the rod, and the sheath being longitudinally disposed relative to the rod of the guide such that an end of the sheath is seated against the foot of the guard, at least one channel of the sheath being laterally aligned with the port of the foot.

6. The discectomy instrument set forth in claim 1 in combination with a cutting tool wherein the cutting tool is detachable from the shaft, and insertable through the channel of the sheath and the port of the guard.

7. The combination set forth in claim 6, wherein the cutting tool is selected from a set of cutting tools that includes a cutting tool that has at least one blade having a sharp edge, and a cutting tool that includes at least one abrasive member.

8. The discectomy instrument set forth in claim 1, wherein the actuator of the guide includes a dial such that rotating the dial in one direction makes the finger more curved along its length and rotating the dial in the opposite direction makes the finger less curved along its length.

9. The discectomy instrument set forth in claim 1, wherein the sheath is positioned between the shaft of the guard and the rod of the guide, the exterior rib of the sheath being inserted into the groove of the rod, and the sheath being longitudinally disposed relative to the rod of the guide such that an end of the sheath is seated against the foot of the guard, at least one channel of the sheath being laterally aligned with the port of the foot.

10. A method for performing a discectomy procedure on a patient using the discectomy instrument set forth in claim 1, the method comprising:
    inserting into the patient the guard;
    positioning the guide relative to the guard;
    positioning the sheath relative to the guard and the guide, the exterior rib being inserted into the groove of the guide, and the sheath being selectively coupled to the shaft of the guard; and
    passing a cutting tool through the channel of the sheath and the port of the guard.

11. The method of claim 10 wherein the sheath comprises a first proximal channel, a second proximal channel, and a distal channel, wherein passing the cutting tool through the channel of the sheath and the port of the guard comprises passing the cutting tool through one of the first proximal channel and the second proximal channel of the sheath such that the cutting tool passes through the distal channel of the sheath and through the port of the guard.

12. A discectomy instrument for use with a cutting tool, the instrument comprising:
    a guard comprising a shaft and a foot extending therefrom, wherein the foot comprises a first surface, a second surface in opposed relationship with the first surface, and a port extending through the foot from the first surface to the second surface and a plurality of teeth extending outward from the second surface;
    a guide comprising a rod, a finger extending from the rod, and an actuator operably connected to the finger such that the finger is selectively articulated via the actuator, the rod including a groove; and
    a sheath comprising a plurality of proximal channels and an exterior rib, the exterior rib being sized and shaped for insertion into the groove of the rod of the guide, the sheath being selectively coupled to the shaft of the guard such that the plurality of proximal channels of the sheath converge into a single distal channel that is laterally aligned with the port in the foot of the guard.

13. The discectomy instrument set forth in claim 12, wherein the foot of the guard includes a tip and a tab disposed on the tip.

14. The discectomy instrument set forth in claim 13, wherein the rod of the guide includes a proximal end and a distal end and a slot located at the distal end, the slot being sized and shaped to receive a tab of the guard.

15. The discectomy instrument set forth in claim 14, wherein the finger of the guide is attached to the distal end of the rod.

16. The discectomy instrument set forth in claim 12 in combination with a cutting tool, the cutting tool being detachable from the shaft and insertable through the channel of the sheath and the port of the guard.

17. The combination set forth in claim 16, wherein the cutting tool is selected from a set of cutting tools that includes a cutting tool that has at least one blade having a sharp edge, and a cutting tool that includes at least one abrasive member.

18. The discectomy instrument set forth in claim 12, wherein the actuator of the guide includes a dial such that rotating the dial in one direction makes the finger more curved along its length and rotating the dial in the opposite direction makes the finger less curved along its length.

\* \* \* \* \*